United States Patent
Nakamura (10) Patent No.: US 9,147,956 B2
(45) Date of Patent: Sep. 29, 2015

(54) HELICAL SPRING, CONNECTOR, ELECTRODE AND ELECTROMETER

(71) Applicant: Tanita Corporation, Tokyo (JP)

(72) Inventor: Yuji Nakamura, Tokyo (JP)

(73) Assignee: TANITA CORPORATION, Tokyo (JP)

( * ) Notice: Subject to any disclaimer, the term of this patent is extended or adjusted under 35 U.S.C. 154(b) by 117 days.

(21) Appl. No.: 13/784,801

(22) Filed: Mar. 4, 2013

(65) Prior Publication Data

US 2014/0103903 A1   Apr. 17, 2014

(30) Foreign Application Priority Data

Oct. 12, 2012   (JP) .................. 2012-227463

(51) Int. Cl.
| | |
|---|---|
| G01R 19/00 | (2006.01) |
| H01R 13/24 | (2006.01) |
| F16F 1/08 | (2006.01) |
| A61B 5/0408 | (2006.01) |

(52) U.S. Cl.
CPC ........ *H01R 13/2421* (2013.01); *A61B 5/04085* (2013.01); *F16F 1/08* (2013.01); *G01R 19/00* (2013.01); *A61B 2562/046* (2013.01)

(58) Field of Classification Search
CPC .............. H01R 13/2421; G01R 19/00; G01R 19/0092; G01R 1/203; G01R 31/2642; F16F 1/08; G06F 9/3802; G06F 2221/2137; G06F 19/34; A61M 16/06; A61M 16/0611; A61M 16/0616; A61M 16/0622; A61M 16/0633; A61N 1/36114; A61N 1/36117; G03G 9/08797; A61B 5/002; A61B 5/04085; A61B 2562/046; A61B 17/0682; B60K 15/03504; E21B 10/25; A23F 3/18

USPC .......... 324/66, 71.1–72.5, 76.11–76.83, 324/84–91, 133; 439/824; 267/166–180; 29/428; 607/115; 156/345.24

See application file for complete search history.

(56) References Cited

U.S. PATENT DOCUMENTS

| | | | | |
|---|---|---|---|---|
| 4,120,489 | A | * | 10/1978 | Borlinghaus .............. 267/166.1 |
| 4,564,436 | A | * | 1/1986 | Buzzanca et al. ............. 204/400 |
| 5,151,040 | A | * | 9/1992 | Tanaka ............................ 439/73 |
| 5,868,383 | A | * | 2/1999 | Codos ............................ 267/80 |

(Continued)

FOREIGN PATENT DOCUMENTS

| | | |
|---|---|---|
| DE | 19935101 A1 | 2/2000 |
| EP | 1527715 A1 | 5/2005 |
| JP | 58177633 | 10/1983 |

OTHER PUBLICATIONS

Extended European Search Report issued in European Application No. 13004547.9 mailed Jan. 3, 2014, 6 pgs.

*Primary Examiner* — Melissa Koval
*Assistant Examiner* — Felicia Farrow
(74) *Attorney, Agent, or Firm* — McDermott Will & Emery LLP (57) ABSTRACT

A helical spring includes cylindrical portions and a widened portion disposed between the cylindrical portions. The cylindrical portions are disposed at both ends of the helical spring in the axis direction and have a constant outside diameter. In the widened portion, from the both ends of the helical spring toward a center of the helical spring in the axis direction, a diameter of the helical spring increases as a pitch of the helical spring increases. The helical spring can be used as part of a connector, an electrode or an electrometer.

12 Claims, 9 Drawing Sheets

(56) References Cited

U.S. PATENT DOCUMENTS

| | | | |
|---|---|---|---|
| 8,186,060 B2 * | 5/2012 | Jee et al. | 29/896.93 |
| 2004/0149384 A1 * | 8/2004 | Kanno et al. | 156/345.24 |
| 2005/0278009 A1 * | 12/2005 | Bona et al. | 607/115 |
| 2006/0202675 A1 * | 9/2006 | Parker et al. | 324/158.1 |
| 2008/0047144 A1 * | 2/2008 | Jee et al. | 29/896.9 |
| 2012/0112396 A1 | 5/2012 | DeFranks et al. | |

* cited by examiner

FIG. 1

AXIS DIRECTION OF HELICAL SPRING

HELICAL SPRING, CONNECTOR, ELECTRODE AND ELECTROMETER

TECHNICAL FIELD

The present invention relates to a helical spring with a small spring constant, a connector having the helical spring and a terminal, an electrode having the connector and a substrate, and an electrometer having the electrode, an arithmetic device and a monitor.

BACKGROUND

In order to measure a potential on a body surface of a patient by using an electrocardiograph, a number of terminals stretching from the substrate of a measurement apparatus generally need to contact the body surface of the patient. The body surface of the patient is unlevel in different manners between patients. When the terminal and the substrate are connected to each other through a usual lead, since a distance therebetween may not be changed according to a shape of the body surface of the patient, it has been difficult to connect a number of terminals to the body surface of the patient. Also, there has been a risk that a connecting part between the terminal and the lead or between the lead and the substrate is disconnected while in use.

As such, Patent Document 1, for example, suggests a technique to connect the terminal and the substrate by using a compression spring. According to this technique, by compressing the compression spring when the terminal is pressed against the body surface of the patient, the distance between the terminal and the substrate is changed, thereby facilitating contact of a number of terminals to the body surface of the patient.

RELATED ART DOCUMENT

Patent Document

Patent Document 1: Japanese Patent Laid-Open No. 58-177633

SUMMARY OF THE INVENTION

Problem to be Solved by the Invention

However, since it is difficult to reduce the spring constant of the compression spring described in Patent Document 1, a heavy load is applied on the patient when the terminal contacts the body surface of the patient, which has been stressful for the patient.

In order to solve such a problem, the present invention provides the helical spring with a small spring constant, the connector, the electrode and the electrometer.

The helical spring according to the present invention is characterized in having the spring constant at 2.0 gf/mm or smaller until being compressed to 50% or more in an axis direction.

This helical spring has the spring constant smaller than that of a conventional helical spring and enables to obtain a larger stroke in response to a small force.

Preferably, the helical spring according to the present invention is wound to have a varied outside diameter and at least a part where adjacent portions in the same phase do not overlap with each other in the axis direction.

In this case, since the adjacent portions in the same phase do not contact with each other in the axis direction, a plurality of rounds of the helical spring may be positioned on one plane perpendicular to the axis direction. Accordingly, a closed height of the helical spring may be reduced.

Also preferably, the helical spring according to the present invention has a larger pitch near a center in the axis direction than the pitch near both ends in the axis direction.

In this case, the helical spring may have a further smaller and approximately constant spring constant.

Here, the helical spring according to the present invention preferably includes cylindrical portions with an approximately constant outside diameter at both ends in the axis direction.

In this case, a large stick member (for example, a terminal) having an outside diameter of approximately the same size as an inside diameter of the cylindrical portion is inserted into the cylindrical portion while being rotated in a direction to open the helical spring, or a cylindrical member having an inside diameter of approximately the same size as an outside diameter of the cylindrical portion is fit on an outside of the cylindrical portion while being rotated in a direction closing the helical spring. Thereby, the member may be easily and strongly fixed to the cylindrical portion of the helical spring.

Next, the connector according to the present invention is characterized in including the helical spring according to the present invention having a conductive property, and a first terminal and a second terminal to respectively fit in the cylindrical portions at both ends of the helical spring.

This connector enables to stably transmit an electric signal while significantly changing a distance between the first terminal and the second terminal.

Preferably, the connector according to the present invention further includes a support connected to the first terminal and stretching in the axis direction of the helical spring.

In this case, buckling (bowing) of the helical spring of the connector may be prevented.

Here, the connector according to the present invention preferably includes the second terminal in a cylindrical shape having the support inserted therein.

In this case, since the support is inserted in the second terminal in the cylindrical shape, the helical spring in a compressed state may be prevented from colliding with the second terminal. Also, a heat capacity of the second terminal may be reduced to facilitate soldering the second terminal to a substrate and the like.

Here, the connector according to the present invention preferably includes the support insulated from the first terminal.

When the support and a second support contact with each other, electricity flows into two routes, possibly changing combined resistance and generating noise. However, insulating the support from the first terminal may prevent generation of such noise.

The electrode according to the present invention is characterized in including a number of connectors according to the present invention and a substrate having a second terminal of each of the connectors fixed thereto.

This electrode enables a number of first terminals to easily contact an uneven plane, as well as enabling to reduce a force received by the plane upon contact.

Here, the electrode according to the present invention preferably includes a plurality of substrates.

In this case, each of the substrates is separately displaced relative to a contact plane of the first terminal. Thereby, a deformation amount of the helical spring is not significantly different between the substrates and, without increasing the stroke of the helical spring more than necessary, the first terminal of the connector fixed to each of the substrates may fit on an uneven contact plane.

One electrometer according to the present invention is characterized in including an electrode according to the present invention, an arithmetic device for performing arithmetic processing of a signal received by the first terminal of the connector of the electrode and calculating a distribution of potentials on the contact plane of the first terminal, and a monitor for displaying the distribution of the potentials calculated by the arithmetic device.

This electrometer enables to reduce a force from the electrode received by the patient, as well as to accurately measure and confirm the potentials at a number of positions on a body surface of the patient.

Another electrometer according to the present invention is characterized in including the electrode, the arithmetic device and the monitor, wherein the electrode includes a helical spring having the spring constant at 2.0 gf/mm or smaller until being compressed to 50% or more in the axis direction. This electrometer may reduce the force from the electrode received by the patient.

The helical spring, the connector, the electrode and the electrometer according to the present invention enable to obtain a large stroke in response to a small force.

BRIEF DESCRIPTION OF THE DRAWINGS

FIG. 3($a$) is a diagram illustrating a relationship between compression amounts in an axis direction of the helical spring according to the present invention and of a conventional compression spring and loads applied on the springs. FIG. 3($b$) is a diagram illustrating a relationship between the compression amount in the axis direction and a spring constant of the helical spring according to the present invention.

DESCRIPTION OF EMBODIMENTS

Embodiments of the present invention will be described as examples with reference to the accompanying drawings.

Figure 1:
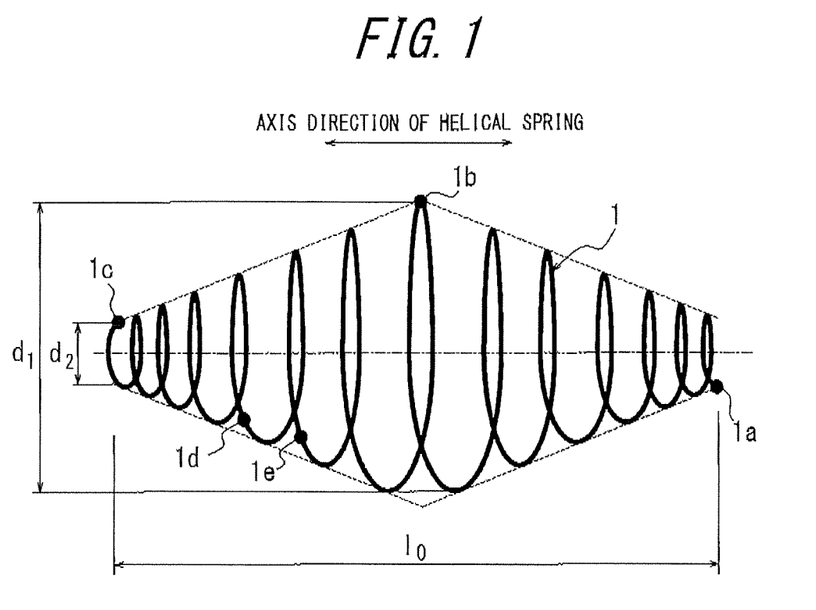
FIG. 1 is a front view of a helical spring according to a first embodiment of the present invention.
Figure 2:
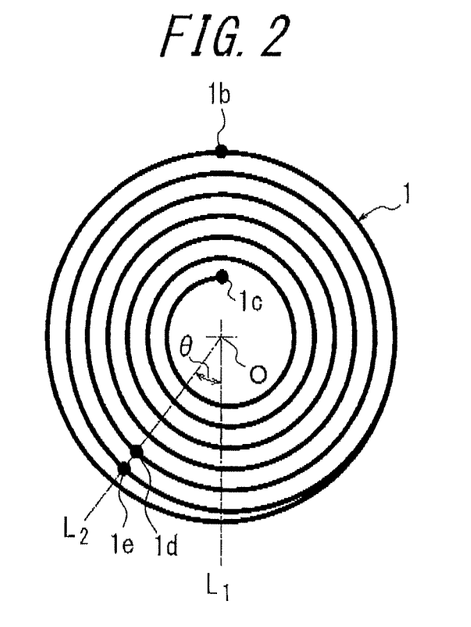
FIG. 2 is a left side view of the helical spring illustrated in FIG. 1.

As illustrated in FIGS. 1 and 2, a helical spring 1 according to a first embodiment of the present invention has an outside diameter gradually increasing from one end 1$a$ to a center 1$b$ in an axis direction and gradually reducing from the center 1$b$ to another end 1$c$ in the axis direction.

Also, the helical spring 1 is wound in such a manner that adjacent portions in the same phase, which are parts 1$d$ and 1$e$ illustrated in FIGS. 1 and 2, for example, do not overlap with each other in the axis direction.

The following is a detailed description of a shape of the helical spring 1. As illustrated in FIG. 2, a straight line $L_1$ connects a center O in the axis direction and a lower side in FIG. 2, and a straight line $L_2$ connects the center O in the axis direction and a position 1$d$ of the helical spring 1. A phase of the 1$d$ is represented by an angle θ between the $L_1$ and the $L_2$. Accordingly, a position 1$e$ adjacent to the same phase as the position 1$d$ is outside the part 1$d$ by one round on an extended line of the $L_2$.

In FIG. 2, the position 1$d$ and the position 1$e$ have no common area and do not overlap with each other in the axis direction.

The helical spring 1 in such a shape may be produced by appropriately adjusting an increase amount of the outside diameter in the axis direction, a pitch angle of the spring, a wire diameter and the like.

Figure 3:
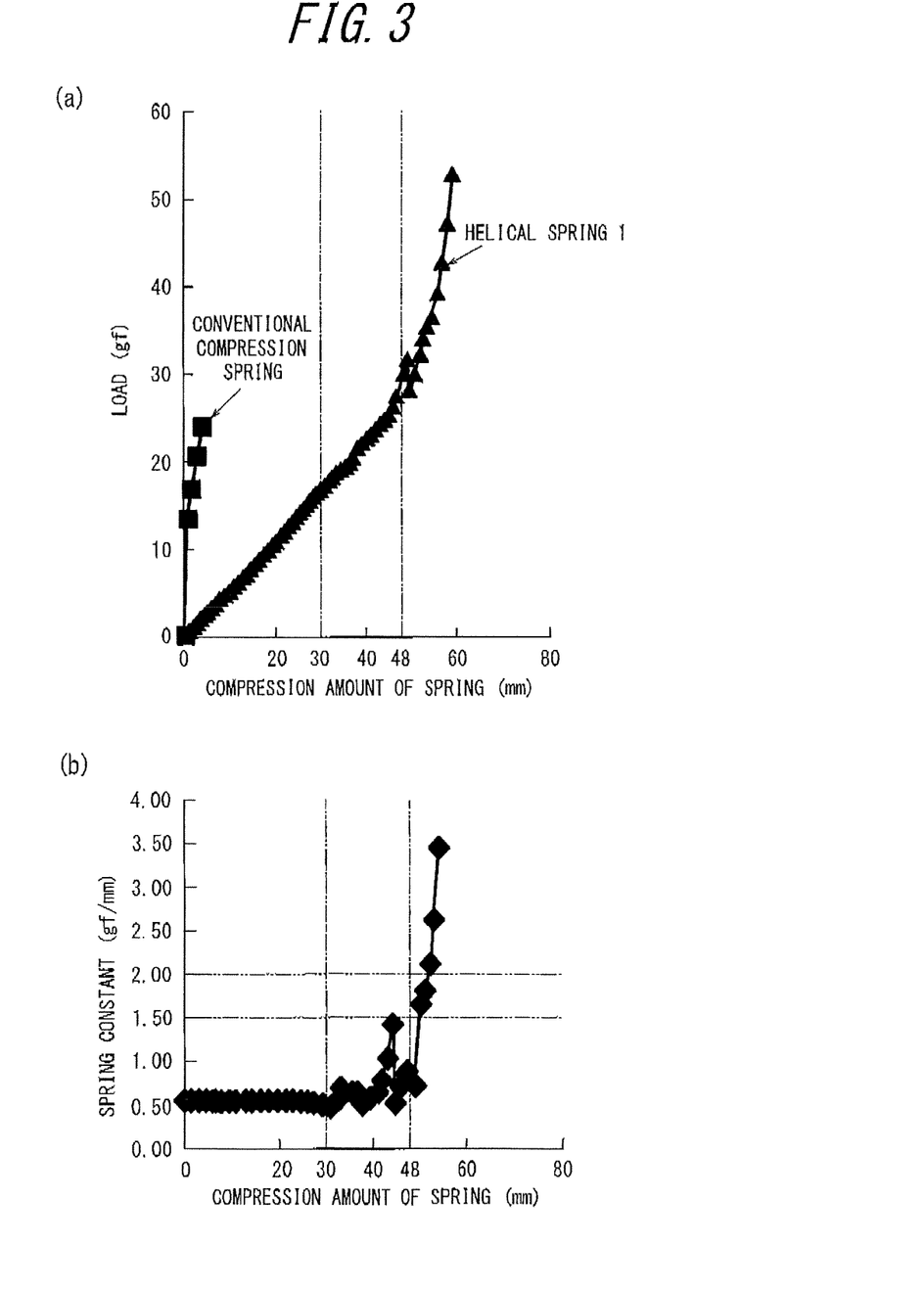

Next, FIG. 3($a$) illustrates a relationship between compression amounts (mm) in the axis direction of the helical spring 1 and of a conventional compression spring and loads (gf) applied on the springs. FIG. 3($b$) illustrates a relationship between the compression amount (mm) in the axis direction and a spring constant (gf/mm) of the helical spring 1.

The helical spring 1 is made of phosphor bronze and is 60 mm in a natural length lo, 8 mm in a maximum outside diameter $d_1$, 3 mm in a minimum diameter $d_2$, and 0.3 mm in the wire diameter (diameter) in FIG. 1.

On the other hand, the conventional compression diameter used for measurement is made of stainless wire SUS304-WPB and is 14 mm in a natural length, 1.06 mm in an outside diameter and 0.1 mm in the wire diameter (diameter).

As can be seen from FIG. 3($a$), the helical spring 1 has a significantly smaller spring constant (a slope of a curve) and a larger compression amount (stroke), in comparison to those of the conventional compression spring. Also, as can be seen from FIG. 3($b$), the helical spring 1 has the spring constant at 2.0 gf/mm or smaller until the compression amount in the axis direction becomes 50% (30 mm in this example) or more (in an area on the left-hand side of a virtual line in the figure).

As can be understood from FIG. 3($b$), the spring constant may be 1.5 gf/mm or smaller. Such a configuration enables to compress the helical spring in response to a smaller force.

When the helical spring is used as an electrode of an electrocardiograph, the spring constant is more preferably at 2.0 gf/mm or smaller until the helical spring is compressed to 80% or more in the axis direction, in order to reduce stress put on a patient.

The following is a description of a reason that the helical spring 1 according to the present embodiment may have a smaller spring constant and a larger stroke in comparison to those of the conventional compression spring. As described above, the helical spring 1 is wound in such a manner that the adjacent portions in the same phase do not overlap with each other in the axis direction. Therefore, when the helical spring 1 is compressed, the adjacent portions in the same phase may be positioned on the same plane perpendicular to the axis direction. Accordingly, a compression allowance of the helical spring 1 is increased, enabling to reduce the spring constant and increase the stroke.

As illustrated in FIG. 1, also, the helical spring 1 is wound to have a larger pitch near the center in the axis direction than that near both ends in the axis direction. Since the pitch of the helical spring 1 is adjusted in this manner, the spring constant may be even smaller and approximately constant in a wide range of the stroke as illustrated in FIG. 3($b$).

Figure 4:
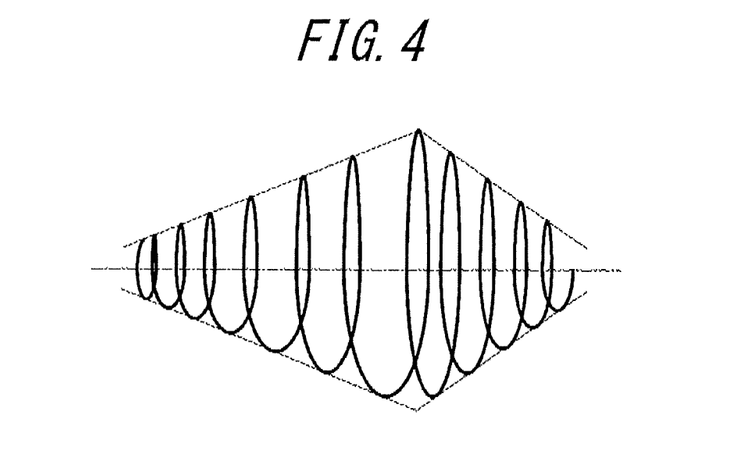
FIG. 4 is a front view illustrating a helical spring according to a second embodiment of the present invention.
Figure 5:
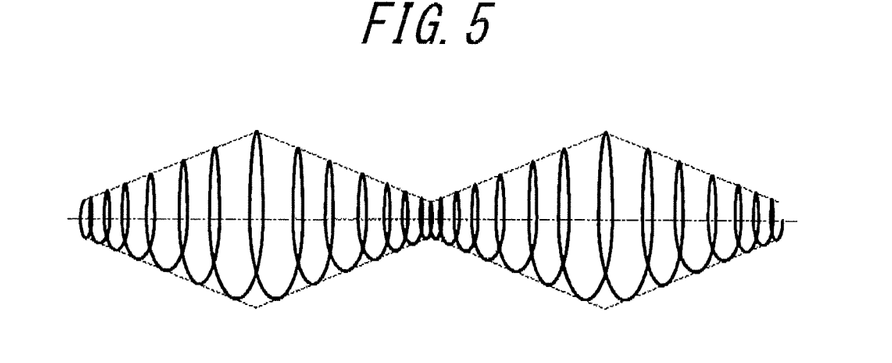
FIG. 5 is a front view illustrating a helical spring according to a third embodiment of the present invention.

Instead of the spring in a barrel shape as illustrated in FIGS. 1 and 2, also in using a conical spring illustrated in FIG. 4 or a gourd-shaped spring illustrated in FIG. 5 wound in such a manner that the adjacent portions in the same phase do not overlap with each other in the axis direction, the spring constant may be reduced and the stroke may be increased.

The helical spring described above is would to have a varied outside diameter and at least a part where the adjacent portions in the same phase do not overlap with each other in the axis direction. Thereby, the spring constant is reduced to be smaller than that of the conventional compression spring. Note that there are other methods to reduce the spring constant of the helical spring. For example, the spring constant may be reduced by using some material or by adjusting the outside diameter and/or the pitch and the like of the helical spring.

Figure 6:
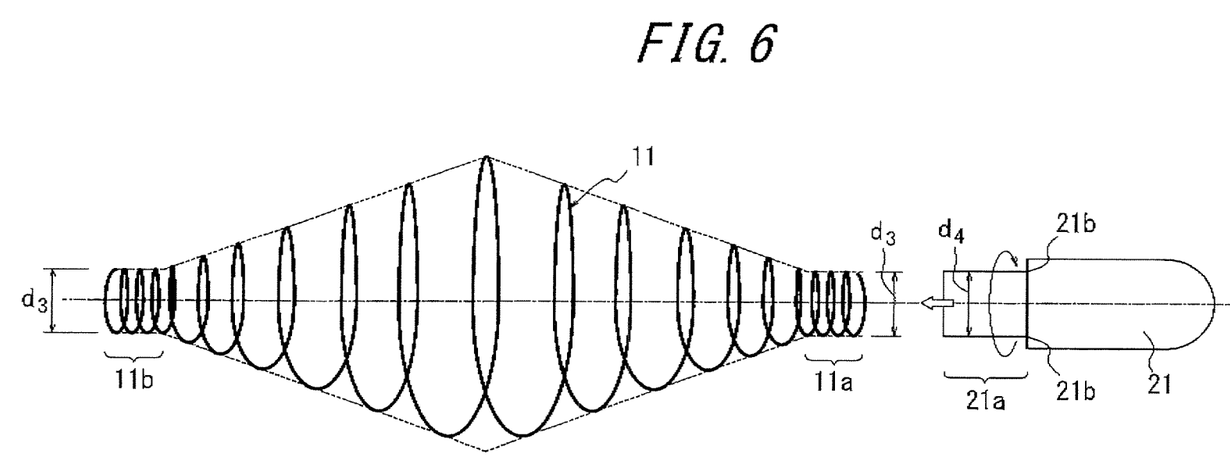
FIG. 6 is a front view illustrating a helical spring according to a fourth embodiment of the present invention.

FIG. 6 illustrates a helical spring 11 according to another embodiment of the present invention. The helical spring 11 has the same configuration as the helical spring 1, except having cylindrical portions 11a, 11b with approximately constant outside diameter at both ends in the axis direction. The spring is wound at a smaller pitch in the cylindrical portions 11a, 11b than in other portions.

Although not illustrated in the figure, the cylindrical portion described above may be provided at only one end of the helical spring 11 in the axis direction. Also, when the cylindrical portions described above are provided at the both ends of the springs in FIG. 4 and FIG. 5, a function effect described below may be obtained.

A stick member such as a terminal 21 having an outside diameter approximately the same as an inside diameter of the cylindrical portions 11a and 11b may be fit in the cylindrical portions 11a and 11b. When a force in the axis direction is applied on the helical spring having the stick member fit therein, the cylindrical portions are hardly deformed in the axis direction. Accordingly, the spring according to the present invention having a cylindrical portion at least one end thereof in the axis direction is defined to have the spring constant at 2.0 gf/mm or smaller until the spring except the cylindrical portion is compressed to 50% or more.

The following is a description of a method to fit the terminal 21 into the cylindrical portion 11a. Although a description is omitted, the terminal 21 may be fit in the cylindrical portion 11b in a similar manner.

Since an outside diameter $d_4$ of a basement 21a is of approximately the same size as an inside diameter $d_3$ of the cylindrical portion 11a, the terminal 21 is resistant to be inserted into the cylindrical portion 11a when the terminal 21 is simply pushed into the cylindrical portion 11a. As illustrated in FIG. 6, however, when the terminal 21 is pushed into the cylindrical portion 11a while being rotated about its axis in a direction expanding the diameter of the cylindrical portion 11a, the inside diameter of the cylindrical portion 11a is expanded and the terminal 21 may be inserted therein by a small force.

An end portion of the terminal 21 from the basement 21a is formed to have an outside diameter larger than the basement 21a. Accordingly, the terminal 21 may be inserted into the cylindrical portion 11a as long as a length of the basement 21a.

Figure 7:
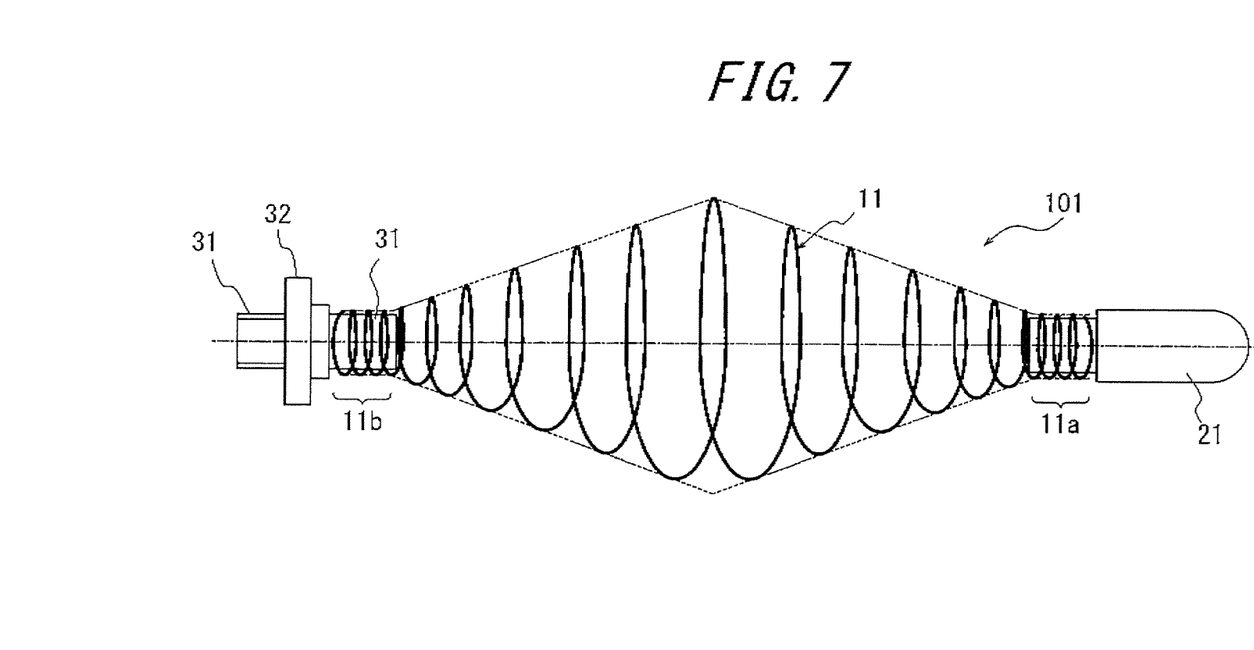
FIG. 7 is a front view illustrating a connector according to the first embodiment of the present invention.

When the terminal 21 is fit in the cylindrical portion 11a as illustrated in FIG. 7, the cylindrical portion 11a having an expanded diameter tries to restore an original outside diameter due to its elastic property. Thereby, the terminal 21 receives a force constricting in a radially inward direction from the cylindrical portion 11a. When the terminal 21 is pulled in a direction to be pulled out of the cylindrical portion 11a, an elastic force of the helical spring 11 acts in an opposite direction. Due to these forces, the terminal 21 is resistant to be pulled out of the cylindrical portion 11a when being simply pulled in the direction to be pulled out of the cylindrical portion 11a.

In order to remove the terminal 21 from the cylindrical portion 11a, the terminal 21 is pulled out of the cylindrical portion 11a while being rotated about its axis in a direction to shrink the diameter of the cylindrical portion 11a (in a direction opposite to that to insert the terminal 21). Thereby, the terminal 21 may be removed from the cylindrical portion 11a by a small force.

Fitting the terminal 21 inside the cylindrical portion 11a in this manner enables to insert, remove and replace the terminal 21 easier in comparison to the terminal 21 fixed by soldering, an adhesive and the like.

Also, although the terminal 21 according to the above embodiment is formed to have a smooth peripheral surface, the peripheral surface may have screw cutting in order to further facilitate insertion, removal and replacement of the terminal 21.

Although not illustrated in the figure, a cylindrical member having an inside diameter of approximately the same as the outside diameter of the cylindrical portion 11a may be fit on the outside of the cylindrical portion 11a. In this case, the cylindrical portion 11a is inserted while the cylindrical member is rotated in the direction closing the helical spring 11, thereby the outside diameter of the cylindrical portion 11a is reduced and thus the cylindrical member may be fit outside the cylindrical portion 11a by a small force.

FIG. 7 illustrates a connector 101 according to the first embodiment of the present invention. The connector 101 includes the helical spring 11 illustrated in FIG. 6 having a conductive property, and the first terminal 21 and the second terminal 31 respectively fit in the cylindrical portions 11a, 11b at both ends of the helical spring 11 in the above manner. The second terminal 31 has a fixing member 32 mounted on an outer periphery near a base thereof for fixing the second terminal 31 to the substrate.

Although not illustrated in the figure, the connector may also be configured by fitting the first terminal 21 in the cylindrical portion at one end of the helical spring according to the present invention and the second terminal to the other end of the helical spring by soldering or another method. Also, the connector may be configured by fixing the first terminal and the second terminal to each of the both ends of the helical spring according to the present invention by soldering or another method.

Here, in order to provide the helical spring 11 with the conductive property, the helical spring 11 is generally made of metal, preferably phosphor bronze (copper alloy) in terms of an electric property. Or, the helical spring 11 may be made of conductive resin, carbon or the like.

Similarly, the first terminal 21 and the second terminal 31 may be made of metal, conductive resin, carbon or the like. In order to provide an antibacterial effect and an antifouling effect to the terminal, one or both of the terminals preferably include photocatalyst such as titanium oxide or the like. Note that the first terminal 21 and the second terminal 31 may be subject to plate processing.

Incidentally, when the connector 101 is used as the electrode of the electrocardiograph, the first terminal 21 may have an end in a dome shape as illustrated in FIG. 7, in a triangular pyramid shape, in a cone shape, in a crown shape, in a flat shape, in a cup shape, or in a diamond (polygonal) shape, to contact at points. Or, the first terminal 21 may have a planarized end.

The connector 101 has the helical spring 11 functioning as a conductive wire for transmitting an electric signal between the first terminal 21 and the second terminal 31. By expanding or compressing the helical spring 11 having a large stroke, the distance between the first terminal and the second terminal may be significantly changed.

Regardless of whether the helical spring 11 is expanded or compressed, the first terminal 21 and the second terminal 31 are strongly fitted in the cylindrical portions 11a and 11b of the helical spring 11, respectively. Therefore, the connector 101 may stably transmit the electric signal.

Figure 8:
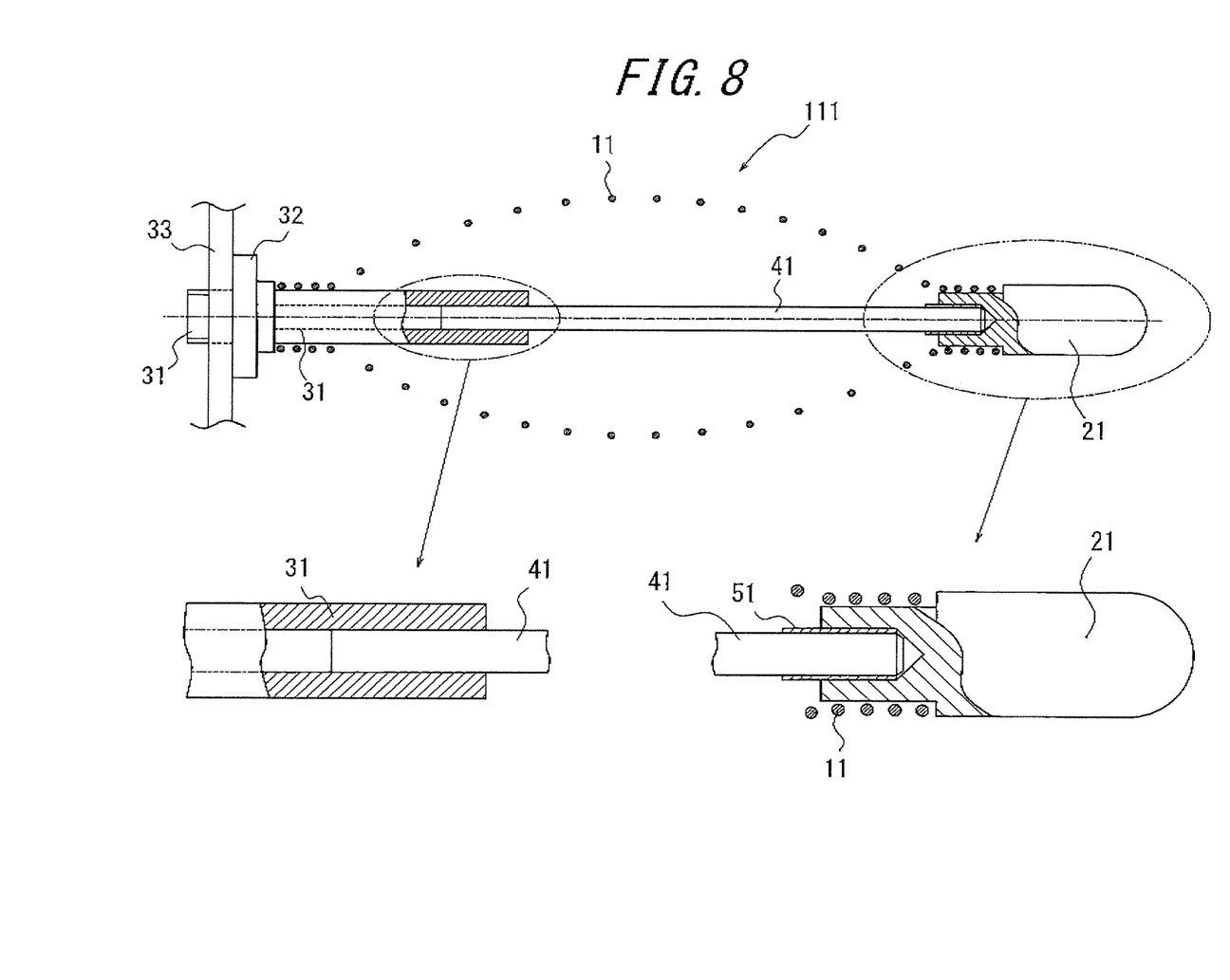
FIG. 8 is a front cross-section view illustrating a connector according to a second embodiment of the present invention.

FIG. 8 illustrates a connector 111 according to a second embodiment of the present invention. The connector 111 has the same configuration as the connector 101 illustrated in FIG. 7, except having a support 41 stretching in the axis direction of the helical spring 11.

Having a small spring constant, the helical spring 11 easily bends in directions perpendicular to the axis direction and is likely to buckle (bow). When the support 41 for connecting the first terminal 21 and the second terminal 31 is provided, such buckling may be prevented.

Here, in order to prevent the support 41 from obstructing expansion and compression of the helical spring 11 in the axis direction, the support 41 and the first terminal 21 or the second terminal 31 may be slidable. In the embodiment illustrated in FIG. 8, the support 41 is inserted into the second terminal 31 in the cylindrical shape so as to be slidable in relation to the second terminal 31.

When the second terminal 31 is in the cylindrical shape and thin as described above, the heat capacity of the second terminal 31 is reduced and temperature thereof easily increases when heated. Thereby, the second terminal 31 may be easily soldered to the substrate 33.

When the support 41 is provided to the connector 111 as illustrated in FIG. 8, the first terminal 21 and the second terminal 31 are connected together via the helical spring 11 and the support 41. Since the helical spring 11 has the conductive property, when the support 41 also has the conductive property, electricity flows in two routes upon contact of the support 41 and the second terminal 31, changing combined resistance and causing noise. As such, when an insulator 51 is provided between the support 41 and the first terminal 21 as illustrated in FIG. 8 such that the support 41 is insulated from the first terminal 21, generation of the noise may be prevented. Note that the support 41 itself may be an insulator to prevent generation of the noise.

Figure 9:
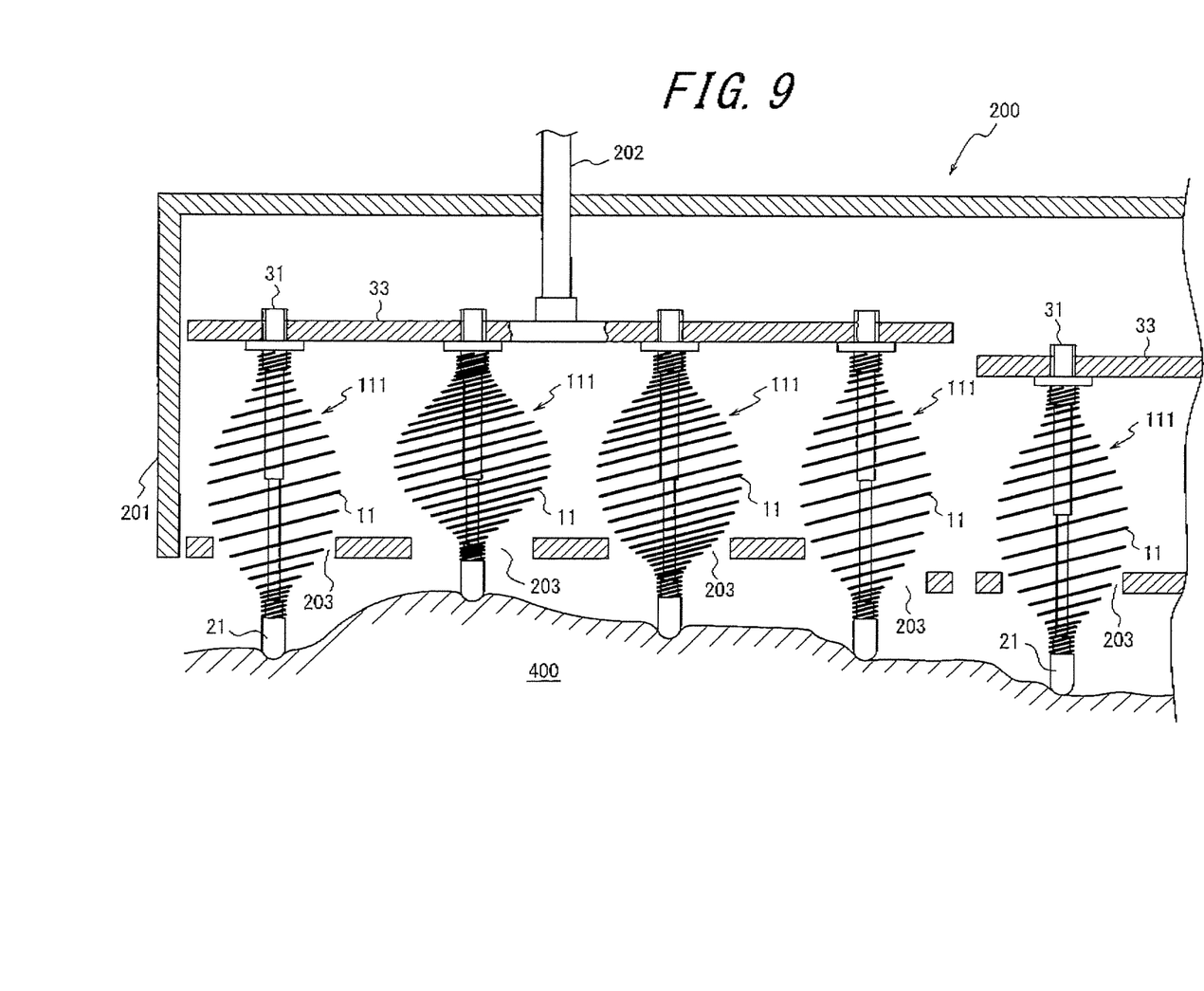
FIG. 9 is a front cross-section view of an electrode according to one embodiment of the present invention.
Figure 10:
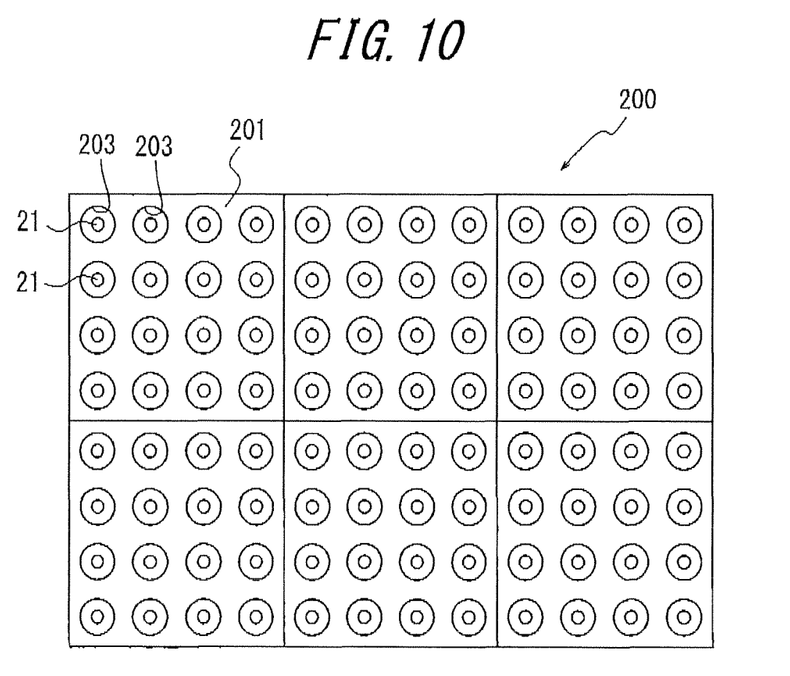
FIG. 10 is a bottom view of the electrode illustrated in FIG. 9.

FIGS. 9 and 10 illustrate an electrode 200 according to one embodiment of the present invention. The electrode 200 is covered with a cover 201 in a box shape. Inside the cover 201, as illustrated in FIG. 9, a plurality of connectors 111 and substrates 33 having the second terminal 31 of each of the connectors 111 soldered thereto are provided in such a manner that the connectors 111 do not contact with each other. An opening 203 is provided on a bottom face of the cover 201 for allowing the first terminal 21 of each of the connectors 111 to protrude therefrom.

Also, the substrate 33 and the bottom face of the cover 201 are separated into a plurality of segments, for example, six segments (3 rows in a longitudinal direction and 2 rows in a width direction) as illustrated in FIGS. 9 and 10. With the substrate 33 and the cover 201 configured in such a manner that each of the segments are separately displaced as described above, when there is significant unevenness on a contact plane 400 of the electrode 200, each segments is displaced along most of the unevenness. Therefore, the helical spring 11 of each connector 111 in each segment needs only to follow fine unevenness. Accordingly, deformation amounts of the helical spring 11 are not significantly different from one another between the segments and, without increasing the stroke of the helical spring 11 more than necessary, the first terminal 21 of each of the connectors 111 may fit on the uneven surface of the contact plane 400.

According to the present embodiment, also, in each segment on the bottom face of the cover 201, the first terminal 21 of the 16 connectors 111 (4 rows both in the longitudinal direction and in the width direction) protrudes from the opening 203. Accordingly, the electrode 200 may receive an input signal from 96 points (6×16). Note that the number of segments and the number of connectors in each segment are not limited to the figures provided above.

The electric signal input to the first terminal 21 of each connector 111 is transmitted, through the helical spring 11, to the substrate 33, to which the second terminal 3l is soldered. A number of input signals collected to the substrate 33 is transmitted to various devices by, for example, a cable 202 penetrating through an upper face of the cover 201 illustrated in FIG. 9.

As illustrated in FIG. 10, the first terminal 21 of each connector 111 protruding from the electrode 200 may be expanded and compressed in the axis direction of the helical spring 11. Accordingly, by pressing the electrode 200 against the contact plane 400 to measure the potential and the like, even when the contact plane 400 is uneven or moves, each of the first terminals 21 of a number of connectors 111 may keep contacting the contact plane 400.

Figure 11:
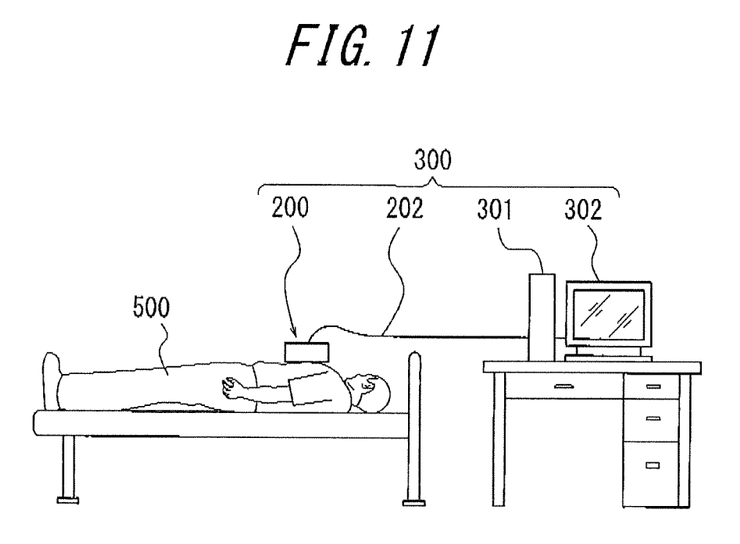
FIG. 11 is a configuration diagram illustrating an electrometer according to one embodiment of the present invention.

As illustrated in FIGS. 3(a) and (b), also, since the helical spring has a very small spring constant, when the helical spring 11 is compressed following the shape of the contact plane 400, the first terminal 21 of each of the connectors 111 has very little influence on the contact plane 400. For example, when the electrode 200 is used as the electrode for the electrocardiograph, the electrode 200 is placed on the chest of the patient as illustrated in FIG. 11. Here, when the electrode 200 weighs 1 kg, the first terminal 21 of each of the connectors 111 receives a force of approximately 10 gf (1000 gf/96) from the body surface of the patient. Since the helical spring 11 has a very small spring constant, the helical spring 11 is significantly deformed by such a small force. Accordingly, each of the first terminals 21 of the connectors 111 may contact the uneven body surface of the patient.

Although the patient receives a force of 1 kgf in total from the first terminals 21 protruding from the electrode 200, such a force generally puts only small stress on the patient.

Accordingly, when the electrode according to the present embodiment is used for the electrocardiograph, the potentials at a number of positions on the body surface of the patient may be measured without heavily stressing the patient.

Note that the electrode described in the above embodiment is a mere example. The electrode having the helical spring with the spring constant at 2.0 gf/mm or smaller until being compressed to 50% or more in the axis direction may substantialize the electrode according to the present invention that enables to obtain a large stroke in response to a small force.

FIG. 11 illustrates an electrometer 300 according to one embodiment of the present invention. According to the present embodiment, the electrometer 300 used as the electrocardiograph includes the electrode 200 illustrated in FIGS. 9 and 10, an arithmetic device 301 for performing arithmetic processing to the signal received by the first terminal 21 of the connector 111 of the electrode 200 and transmitted through the cable 202 and calculating the distribution of the potentials on the contact plane of the first terminal 21, and a monitor 302 for displaying the distribution of the potentials calculated by the arithmetic device 301.

By using the electrometer 300, the distribution of the potentials on a surface of the chest of a patient 500 in the supine position may be measured. In measuring, the electrode 200 is placed on the chest. Here, the electrode 200 is not pressed against the chest of the patient 500 by applying a force on an upper face of the electrode 200 but the weight of the electrode 200 alone is applied on the chest of the patient 500, thereby the stress applied on the patient may be reduced.

Although the chest of the patient generally has unevenness due to the breasts or muscles, the helical spring 11 of each connector 111 of the electrode 200 is compressed along the uneven surface of the chest of the patient due to the weight of the electrode 200 such that each of the first terminals 21 of the connectors 111 contacts the chest of the patient.

In the above manner, the electrode 200 may receive the electric signals at a number of positions on the body surface of the patient 500.

The electric signal received by the first terminal 21 of the electrode 200 is transmitted to the arithmetic device 301 via the cable 202. The arithmetic device 301, from the received electric signal, creates a map of the potentials on the chest of the patient 500. The map of the potentials is output to the monitor 302 to be used for an examination by a doctor.

Note that the electrometer according to the above embodiment is a mere example. The electrometer having the electrode that has the helical spring with the spring constant at 2.0 gf/mm or smaller until being compressed to 50% or more in the axis direction may substantialize the electrometer according to the present invention that reduces the force from the electrode received by the patient. Also, the electrometer according to the present invention may have the arithmetic device, the monitor and the electrode that are integrally configured.

EXPLANATION OF REFERENCE NUMERALS

1 Helical spring
1a End
1b Center in axis direction
1c, 1d Portion
2 Width direction
11 Helical spring
11a, 11b Cylindrical portion
21 First terminal
21a Basement
31 Second terminal
32 Fixing member
33 Substrate
41 Support
51 Insulator
101, 111 Connector
200 Electrode
201 Cover
202 Cable
203 Opening
300 Electrometer
301 Arithmetic device
302 Monitor
400 Contact plane
500 Patient

What is claimed is:

1. A helical spring, comprising: cylindrical portions, with a constant outside coil diameter between successive coils, disposed at both ends of the helical spring in the axis direction; and a widened portion disposed between the cylindrical portions, wherein in the widened portion, from the both ends of the helical spring toward a center of the helical spring in the axis direction, a diameter of the helical spring increases as a pitch of the helical spring increases, wherein the helical spring is formed from a conducting material.

2. The helical spring according to claim 1, where the helical spring has a spring constant at 2.0 gf/mm or smaller until being compressed to 50% or more in an axis direction.

3. A connector comprising: the helical spring according to claim 1 with a conductive property; and a first terminal and a second terminal to respectively fit in the cylindrical portions at the both ends of the helical spring, wherein the helical spring transmits an electrical signal between the first terminal and the second terminal.

4. The connector according to claim 3, further comprising a support connected to the first terminal and stretching in the axis direction of the helical spring.

5. The connector according to claim 4, wherein the second terminal is in the cylindrical shape and having the support inserted therein.

6. The connector according to claim 4, wherein the support is insulated from the first terminal.

7. An electrode comprising:
a plurality of connectors each according to claim 3; and
a substrate having the first terminal or the second terminal of each of the connectors fixed thereto.

8. The electrode according to claim 7 having a plurality of substrates.

9. An electrometer comprising:
the electrode according to claim 7;
an arithmetic device for performing arithmetic processing to a signal received by the first terminal of the connector of the electrode and calculating a distribution of potentials on a contact plane of the first terminal; and
a monitor for displaying the distribution of the potentials calculated by the arithmetic device.

10. An electrometer comprising: an electrode; an arithmetic device; and a monitor, wherein the electrode includes the helical spring according to claim 1.

11. The connector according to claim 3, wherein:
the widened portion has a barrel shape, and
the cylindrical portions are provided at portions having a minimum diameter of the helical spring and have an inside diameter the same as an outside diameter of the second terminal.

12. The connector according to claim 4, wherein the support and the first terminal or second terminal are slidable.

* * * * *